United States Patent [19]

Chu et al.

[11] Patent Number: 4,871,866

[45] Date of Patent: Oct. 3, 1989

[54] LYSOCELLIN SOLIDS PURIFICATION PROCESS

[75] Inventors: Alexander H. T. Chu; M. James Levi, both of Terre Haute, Ind.

[73] Assignee: Pitman-Moore, Inc., Terre Haute, Ind.

[21] Appl. No.: 88,293

[22] Filed: Aug. 24, 1987

[51] Int. Cl.[4] .................. C07D 407/00; C07D 407/14
[52] U.S. Cl. .................................... 549/414; 424/123; 435/118; 435/803; 435/886; 549/385
[58] Field of Search .................. 435/118, 886, 803; 549/385, 414; 424/123

[56] References Cited

U.S. PATENT DOCUMENTS

| | | | |
|---|---|---|---|
| 4,033,823 | 7/1977 | Liu et al. | 435/118 |
| 4,478,935 | 10/1984 | Williams et al. | 435/75 |
| 4,693,992 | 9/1987 | Young | 514/11 |
| 4,746,650 | 5/1988 | Cullen et al. | 514/27 |

OTHER PUBLICATIONS

Ebata et al., *J. Antibiotics*, 28:118 (1975).

*Primary Examiner*—Paul Lieberman
*Assistant Examiner*—Linda D. Skaling
*Attorney, Agent, or Firm*—Wendell Ray Guffey; Thomas L. Farquer

[57] ABSTRACT

A process for purifying lysocellin which comprises mixing lysocellin solids with sufficient halogen acid to convert fatty acid ester salt impurities into water-soluble metal halogen salts and water-insoluble free fatty acids and to convert lysocellin salts into water-soluble metal halogen salts and water-insoluble lysocellin acid, separating the halogen salts from the lysocellin acid and fatty acid solids, mixing the lysocellin acid and fatty acid solids with sufficient caustic reagent to convert free fatty acids into water-soluble alkali metal salts and to convert lysocellin acid into a water-insoluble alkali metal lysocellin salts, and separating the water-soluble fatty acid alkali metal salts from the alkali metal lysocellin solids.

19 Claims, No Drawings

LYSOCELLIN SOLIDS PURIFICATION PROCESS

This invention relates generally to processes for purifying polyether antibiotics and particularly to a process for purifying lysocellin solids containing impurities in the form of fatty acids and fatty acid ester salts formed from undesirable metal cations.

BACKGROUND OF THE INVENTION

Lysocellin is a divalent polyether antibiotic produced by culturing Streptomyces type microorganisms. Polyether antibiotics as a class are reviewed in Westley, *Adv. Appl. Microbiology.* 22:177–223 (1977). Westley classified lysocellin in Class 2a; Class 2a antibiotics have a generally linear configuration, may contain from about two to about three tetrahydropyran and/or -furan structures, up to about three tetrahydropyran and/or -furan structures, up to about three total ring structures and no nitrogen atoms. The isolation and purification of polyether antibiotics using extraction methods have been extensively reviewed in Hamill et al., "Polyether Antibiotics" pp. 479–520, *J. Chromatogr. Lib.*, Vol. 15. Antibiotics: Isolation, Separation, and Purification, ed. by Weinstein, M. J. and Wagman, G. H. (1978).

Procedures for producing, isolating, and purifying lysocellin are known in the art. Lysocellin is generally produced by fermenting a nutrient-containing liquid fermentation medium or broth inoculated with a microorganism capable of producing the desired antibiotic. Suitable liquid fermentation media are generally aqueous dispersions containing sources of assimilable nitrogen and carbon as is known in the art. The fermentation media can also contain a variety of optional ingredients, if desired, such as for example, pH adjustment agents, buffers, trace minerals, antifoam agents, and the like.

Known methods for recovering lysocellin from fermentation broths generally involve multi-stage organic solvent extractions and related filtration, chromatography, concentration, and crystallization operations. The procedure to isolate and purify lysocellin was first described in Ebata et al., *J. Antibiotics,* 28:118–121 (1975). Ebata used a multi-step organic extraction process which incorporated acetone, n-butanol, methanol, and the like. U.S. Pat. No. 4,033,823 describes an extraction process for recovering lysocellin which incorporates ethyl acetate, acetonitrile, hexane and methanol. U.S. Pat. No. 4,478,935 describes various purified manganese-containing antibiotic complexes extracted from the dried biomass using suitable organic solvents followed by crystallization or precipitation of the complexes. All of these processes follow a rather standard approach in which fermentation broths are subjected to organic solvent extraction to recover the lysocellin as a crystalline solid.

Production of lysocellin by these procedures produces, as a general rule, relatively pure lysocellin solids which can be used commercially. However, some fermentation batches produce lysocellin solids which contain large amounts of impurities in the form of fatty acids or fatty acid ester salts formed from undesirable metal cations, particularly fatty acid ester salts formed with metal cations such as magnesium, calcium, iron, and the like. These fatty acid ester salts containing metal ion impurities often result when fermentation broths or nutrients contain high levels of these metal ions, although many other sources can contaminate the broth. The presence of large amounts of these fatty acid or ester salts make the lysocellin solids produced from the lysocellin production process unusable for their intended purpose.

Prior methods for removing these impurities have generally involved organic extraction procedures in which the impurities and lysocellin are separated based upon their differing solubilities in various organic solvents. The problem has been that, as with all extraction procedures, a portion of the solubilized lysocellin is lost during the solubilization and extraction procedure. The lysocellin lost during the extraction decreases the yield in the purification procedure. More often, because of these difficulties, lysocellin solids containing large amounts of impurities are merely discarded.

In addition, because the sodium form of lysocellin is very stable in a variety of environments, sodium lysocellin is more suitable than other salts for animal feed applications. However, since calcium, magnesium, iron, and other metal ions may exhibit greater affinity to the divalent lysocellin ionophore than sodium for lysocellin concentrations higher than 1.5 g/L (Mitani et al., *J. Antibiotics,* 30, 186–88, 1977), it is difficult to isolate lysocellin in the sodium form once other salts have been formed during fermentation.

There has not been an effective process for separating lysocellin from these impurities, fatty acids and fatty acid ester salts, in which the lysocellin is not solubilized in an extraction procedure. A procedure in which the lysocellin remains in a solid form, not solubilized, would avoid the accompanying loss of lysocellin resulting from the solubilization in the purification procedure. A method is, therefore, needed which can purify lysocellin solids by solubilizing and removing fatty acid and fatty acid ester salt impurities while maintaining the lysocellin as a solid.

SUMMARY OF THE INVENTION

It is, therefore, an object of the present invention to provide a process for purifying lysocellin solids.

It is another object of the present invention to provide a process for purifying lysocellin solids by removing impurities such as fatty acids and fatty acid ester salts formed by undesirable metal cations.

It is a further object of the present invention to provide a process for purifying lysocellin solids in which lysocellin remains a solid and the impurities are solubilized and removed.

It is another object of the present invention to provide a process for purifying lysocellin solids which avoids the loss of lysocellin which accompanies solvent extraction purification procedures.

It is another object of the present invention to provide a process for purifying lysocellin solids in which the lysocellin in recovered as alkali metal lysocellin.

It is a further object of the present invention to provide a process for purifying lysocellin solids in which the lysocellin in recovered as sodium lysocellin.

These and other objects are achieved by mixing lysocellin solids containing impurities in the form of fatty acids and fatty acid ester salts with sufficient halogen acid to convert the fatty acid and fatty acid ester salt impurities into water-soluble metal halogen salts and water-insoluble free fatty acids and to convert the lysocellin salts into water-soluble metal halogen salts and water-insoluble lysocellin acid, separating the aqueous solution containing the halogen salts from the lysocellin acid and fatty acid solids, mixing the lysocellin acid and fatty acid solids with sufficient caustic reagent to convert the free fatty acids into water-soluble alkali metal salts and to convert the lysocellin acid into water-insoluble alkali metal lysocellin salts, and separating the aqueous solution containing the water-soluble fatty acid alkali metal salts from the alkali metal lysocellin solids to produce a purified lysocellin product containing a high percentage of alkali metal lysocellin, greater than 90%, and a low percentage of impurities, less than 10%, in the form of fatty acids and fatty acid ester salts.

In the preferred embodiment, lysocellin solids containing impurities in the form of fatty acids and fatty acid ester salts are mixed with sufficient hydrochloric acid (HCl) to bring the pH of the solution to from about 1 to about 5. The lysocellin acid and fatty acid solids are separated from the water-soluble metal halogen salts as above and mixed with sufficient caustic in the form of sodium hydroxide (NaOH) to bring the pH of the solution to from about 10 to about 14. The purified lysocellin solids are recovered as above and used for their intended purpose.

Other objects, advantages, and novel features of the present invention will become apparent from the following detailed description of the invention.

DETAILED DESCRIPTION OF THE INVENTION

As used herein, the term "halogen acid" is defined as the hydrogen compounds of the halogens.

As used herein, and the term "caustic reagent" is defined as the hydroxides of the alkali metals.

As used herein, the term "lysocellin solids" is defined to include the solid product resulting from fermentation processes designed to produce lysocellin. "Lysocellin solids" typically contain lysocellin acid, lysocellin salts, free fatty acids, fatty acid ester salts, and other impurities. The fatty acids are inherently present due to the soybean oil and various fatty acids added as nutrients during fermentation and the corn oil and/or other glycerides added to recover lysocellin crystals from fermentation products. The metal ions that form the fatty acid ester salts and the lysocellin salts, typically magnesium, calcium, iron, are often in contaminated water or nutrient materials used in the fermentation process. The metal ions, of course, can come from many different sources of contamination.

According to the present invention, a process is provided for purifying lysocellin solids containing impurities in the form of fatty acids and fatty acid ester salts formed from undesirable metal cations. The process comprises mixing lysocellin solids containing the impurities with sufficient halogen acid to convert the fatty acids and fatty acid ester salt impurities into water-soluble metal halogen salts (such as $CaX_2$, $MgX_3$, $FeX_3$ and the like, where X is a halogen) and water-insoluble free fatty acids and to convert the lysocellin salts into water-soluble metal halogen salts and water-insoluble lysocellin acid, separating the aqueous solution containing the halogen salts from the lysocellin acid and fatty acid solids, mixing the lysocellin acid and fatty acid solids with sufficient caustic reagent to convert the free fatty acids into water-soluble alkali metal salts and to convert the lysocellin acid into water-insoluble alkali metal lysocellin salts, and separating the aqueous solution containing the water-soluble fatty acid alkali metal salts from the alkali metal lysocellin solids to produce a purified lysocellin product containing a high percentage of alkali metal lysocellin, greater than 90%, and a low percentage of impurities, less than 10%, in the form of fatty acids and fatty acid ester salts.

Impurities, particularly in the form of fatty acids and fatty acid ester salts, in lysocellin solids result from many causes; typical causes include (1) lysocellin fermentation batches produced using water containing high levels of calcium, magnesium, iron, and the like, (2) excess fatty acids being present during the fermentation and recovery process, and (3) fatty acid ester salts which result from the combination of the metal ions and the excess free fatty acids. Also, fatty acids are often added to induce the formation of "aggregates" containing the lysocellin solids. The production, recovery, and purification processes and the problems of impurities associated therewith are well known in the art.

The lysocellin solids are mixed with a halogen acid. Sufficient halogen acid is added to bring the pH of the solution to from about 1 to about 5, preferably from about 1 to about 3, and most preferably about 2. The halogen acid converts the fatty acid ester salt impurities into water-soluble metal halogen salts and water-insoluble free fatty acids and converts the lysocellin salts into water-soluble metal halogen salts and water-insoluble lysocellin acid, The halogen acids are preferably hydrochloric acid (HCl) and hydrobromic acid (HBr), most preferably HCl. Other acids such as sulfuric acid ($H_2SO_4$) or phosphoric ($H_3PO_4$) will not function in the present invention since they convert the fatty acid ester salt impurities into a water-insoluble salt (e.g. $CaSO_4$ or $Ca_3(PO_4)_2$) which cannot be separated from the lysocellin solids.

The solid lysocellin acid is separated from the solution containing the soluble metal chlorides by any acceptable means such as decantation, filtration, centrifugation, and the like. Filtration is preferred because of the speed of the process and the ability to handle large quantities of materials. The filtrate containing the water-soluble impurities (e.g. $CaCl_2, MgCl_2, FeCl_3$) is discarded and the solids are saved for further processing.

The resulting lysocellin solids are subjected to a caustic treatment. Sufficient caustic reagent is added to bring the pH of the solution to from about 10 to about 14, preferably about 12. The caustic reagent converts the free fatty acids into water-soluble alkali metal salts and converts lysocellin acid into a water-insoluble alkali metal lysocellin salts. The caustic reagents are preferably sodium hydroxide (NaOH) and or potassium hydroxide (KOH), most preferably NaOH.

The solids containing the alkali metal salts of the fatty acid and lysocellin are washed with water to solubilize the residual fatty acid alkali metal salts. The water-insoluble alkali metal lysocellin is separated from the soluble fatty acids and fatty acid alkali metal salts by any acceptable means such as decantation, filtration, centrifugation, and the like. Filtration is preferred because of the speed of the process and the ability to handle large quantities of materials. The filtrate containing the impurities (e.g. sodium oleate, sodium linoleate) is discarded and the solids are saved. This washing procedure may be repeated several times to remove all the impurities. Other solvents such as methanol, ethanol, and the like could also be used but are not preferred since alkali metal lysocellin is more soluble in these solvents than in water. The resulting product is a purified lysocellin solids containing a high percentage (>90%) of alkali metal lysocellin and a low percentage (<10%) of impurities, particularly in the form of fatty acids and fatty acid ester salts.

In the preferred embodiment, lysocellin solids containing impurities in the form of fatty acids and fatty acid ester salts are mixed with hydrochloric acid (HCl) to convert the fatty acid ester salt impurities into water-soluble metal chloride salts (such as $CaCl_2$, $MgCl_3$, $FeCl_3$ and the like) and water-insoluble free fatty acids and to convert the lysocellin salts into water-soluble chloride salts and water-insoluble lysocellin acid. Sufficient HCl is added to bring the pH of the solution to from about 1 to about 5, preferably from about 1 to about 3, and most preferably about 2. The lysocellin acid and fatty acid solids are separated as above and mixed with sodium hydroxide (NaOH) to convert the free fatty acids into water-soluble sodium salts and to convert the lysocellin acid into water-insoluble sodium lysocellin salts. Sufficient NaOH is added to bring the pH of the solution to from about 10 to about 14, preferably about 12. The purified lysocellin solids are recovered and used as desired, typically as growth promotants in cattle and other animals.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1

An off-spec lysocellin batch (Batch F30–6L, purity 84.4%) produced using the lysocellin production process described in U.S. patent application Ser. No. 868,015, incorporated herein by reference, was contaminated with large amount of calcium (2600 ppm) from process water. A laboratory experiment was conducted to purify the material using HCl. The lysocellin solids were acidified to pH 2 and mixed for more than an hour; the resulting solution containing free fatty acids and lysocellin acid was filtered to remove water-soluble $CaCl_2$. The resultant solids were saponified for sodium conversion and oil separation for three hours at pH 12. The filtered cake was water washed twice and dried. About 96% calcium was removed at a 101% mass balance yielding only 131 ppm calcium in the final lysocellin product. Final purity by bioassay was 96% at a 95.9% recovery.

EXAMPLE 2

Crude lysocellin solids produced in the pilot plant (Batch F30–8L) using the lysocellin production process described in U.S. patent application Ser. No. 868,015, incorporated herein by reference, contained a large amount of calcium (841–1700ppm). The sodium contents were lower than the 3.20% specification (the theoretical content for pure Na-lysocellin is 3.49%). The calcium salt of lysocellin has been shown to exhibit only about 85% bioactivity as compared to both sodium and potassium salts. To upgrade the product quality, five fractions were combined and treated with aqueous HCl solution at pH 2 for about an hour. The acid solution was filtered, and the solids mixed with $NaOH_{(aq)}$ solution at pH 12 for three hours for sodium conversion and oil saponification. The mixture was then vacuum filtered, water washed, and vacuum dried (28" Hg, 120F) to obtain the purified lysocellin product. The results are shown in Table 1.

Referring to Table 1, the results show that the purity was increased from an average of 94.6% to 99.9%, the sodium content improved to 3.43%, and calcium content reduced to 34 ppm.

EXAMPLE 3

Crude lysocellin solids produced in the pilot plant (Batch F30–10L) using the lysocellin production process described in U.S. patent application Serial No. 868,015, incorporated herein by reference, contained high residual oil, high calcium, and low sodium. The crude lysocellin solids were dispersed in $HCl_{(aq)}$ solution for an hour to convert lysocellin salts into the free acid form and the undesirable fatty acid or ester salts into water-soluble chlorides which were removed by filtration. The solids containing lysocellin acid and residual oil were then mixed with dilute NaOH solution at pH 12–14 for one to three hours and then vacuum filtered. The resultant filter cake was further washed with deionized water for removing residual fatty acid sodium salts and caustic content. The results for each of the two replicates are shown in Table 2.

Referring to Table 2, the data show that the oil and Ca contents in the final, dried product were reduced and sodium content increased. An 89.8% step recovery was achieved at a 94% mass balance.

Obviously many modifications and variations of the present invention are possible in light of the above teachings. It is therefore to be understood that within the scope of the appended claims the invention may be practiced otherwise than as specifically described.

TABLE 1

| Batch No. | Before HCl Treatment | | | | | After HCl and NaOH Treatments |
|---|---|---|---|---|---|---|
| | 8L-37 | 8L-39 | 8L-40 | 8L-41 | 8L-45 | 8L-Composite |
| Lysocellin Purity % | 93.9 | 94.8 | 96.3 | 91.3 | 89.6 | 104.4 |
| Oil (GC) % | 3.0 | 0.9 | 0.4 | 0.7 | 0.8 | 1.0 |
| Na % | 3.09 | 3.20 | 3.06 | 3.08 | 3.02 | 3.43 |
| Ca % | 0.17 | 0.12 | 0.13 | 0.0885 | 0.0841 | 0.034 |
| K % | 0.0040 | 0.0006 | 0.0015 | 0.0011 | 0.0006 | <0.001 |
| Mg % | 0.0387 | 0.0180 | 0.0163 | 0.0134 | 0.0130 | 0.001 |
| Fe % | 0.0038 | 0.0083 | 0.0022 | 0.0055 | 0.0064 | 0.003 |
| Weight (kg) | 7.95 | 2.93 | 15.18 | 2.22 | 2.27 | 22.93 |
| % Step Recovery | | | | | | 79.3% |
| % Mass Balance | | | | | | 81.1% |

TABLE 2

| Batch No. | Before HCl 10L-71 | After HCl & NaOH 10L-93 |
|---|---|---|
| % Lysocellin Purity | 98.15 | 101.76 |
| % Oil (GC) | 4.1 | 2.16 |
| % Na | 3.08 | 3.62 |

TABLE 2-continued

| Batch No. | Before HCl 10L-71 | After HCl & NaOH 10L-93 |
| --- | --- | --- |
| % Ca | 0.14 | 0.0347 |
| % K | <0.001 | <0.001 |
| % Mg | 0.179 | 0.0032 |
| % Fe | 0.0048 | 0.0069 |
| Weight (kg) | 5.0 | 4.4 |
| % Step Recovery | | 89.8% |
| % Mass Balance | | 94.0% |

What is claimed is:

1. A lysocellin purification process suitable for removing fatty acid and fatty acid ester salt impurities from lysocellin solids, consisting essentially of the steps of:
    mixing lysocellin solids containing the impurities with sufficient halogen acid to convert the fatty acid ester salt impurities into water-soluble metal halogen salts and water-insoluble free fatty acids and to convert the lysocellin salts into water-soluble metal halogen salts and water-insoluble lysocellin acid;
    separating the aqueous solution containing the halogen salts from the lysocellin acid and fatty acid solids;
    mixing the lysocellin acid and fatty acid solids with sufficient caustic reagent to convert the free fatty acids into water-soluble alkali metal salts and to convert the lysocellin acid into a water-insoluble alkali metal lysocellin salts; and
    separating the aqueous solution containing the water-soluble fatty acid alkali metal salts from the alkali metal lysocellin solids, thereby producing a purified lysocellin product containing greater than 90% alkali metal lysocellin and less than 10% impurities in the form of fatty acids and fatty acid ester salts.

2. The process of claim 1 wherein the halogen acid is hydrochloric acid (HCl) or hydrobromic acid (HBr).

3. The process of claim 1 wherein the halogen acid is mixed with the lysocellin solids in amounts sufficient to produce a pH of between about 1 to 5.

4. The process of claim 3 wherein the halogen acid is hydrochloric acid (HCl).

5. The process of claim 1 wherein the separating steps are filtration steps.

6. The process of claim 1 wherein the caustic reagent is sodium hydroxide (NaOH) or potassium hydroxide (KOH).

7. The process of claim 1 wherein the caustic reagent is mixed with the lysocellin acid and fatty acid solids in amounts sufficient to produce a pH of between about 10 to about 14.

8. The process of claim 7 wherein the caustic reagent is sodium hydroxide (NaOH).

9. The process of claim 1 wherein the fatty acid ester salts are magnesium, calcium, and iron fatty acid ester salts.

10. A lysocellin purification process suitable for removing fatty acid and fatty acid ester salt impurities from lysocellin solids consisting essentially of the steps of:
    mixing lysocellin solids containing the impurities with sufficient hydrochloric acid (HCL) to convert the fatty acid ester salt impurities into water-soluble metal chloride salts and water-insoluble free fatty acids and to convert the lysocellin salts into water-soluble metal chloride salts and water-insoluble lysocellin acid;
    separating the aqueous solution containing the chloride salts from the lysocellin acid and fatty acid solids;
    mixing the lysocellin acid and fatty acid solids with sufficient sodium hydroxide (NaOH) to convert the free fatty acids into water-soluble sodium salts and to convert the lysocellin acid into a water-insoluble sodium lysocellin salts; and
    separating the aqueous solution containing the water-soluble fatty acid sodium salts from the sodium lysocellin solids, thereby producing a purified lysocellin product containing greater than 90% alkali metal lysocellin and less than 10% impurities in the form of fatty acids and fatty acid ester salts.

11. The process of claim 10 wherein the HCl is mixed with the lysocellin solids in amounts sufficient to produce a pH of between about 1 to 5.

12. The process of claim 10 wherein the separating steps are filtration steps.

13. The process of claim 10 wherein the caustic reagent is mixed with the lysocellin acid and fatty acid solids in amounts sufficient to produce a pH of between about 10 to about 14.

14. The process of claim 10 wherein the fatty acid ester salts are magnesium, calcium, and iron fatty acid ester salts.

15. A lysocellin purification process suitable for removing fatty acid and fatty acid ester salt impurities from lysocellin solids, consisting essentially of the steps of:
    mixing lysocellin solids containing the impurities with sufficient hydrochloric acid (HCl) to produce a pH of between about 1 to 5, thereby converting the fatty acid ester salt impurities into water-soluble metal chloride salts and water-insoluble free fatty acids and converting the lysocellin salts into water-soluble metal chloride salts and water-insoluble lysocellin acid;
    separating the aqueous solution containing the chloride salts from the lysocellin acid and fatty acid solids;
    mixing the lysocellin acid and fatty acid solids with sufficient sodium hydroxide (NaOH) to produce a pH of between about 10 to about 14, thereby converting the free fatty acids into water-soluble sodium salts and converting the lysocellin acid into a water-insoluble sodium lysocellin salts; and
    separating the aqueous solution containing the water-soluble fatty acid sodium salts from the sodium lysocellin solids, thereby producing a purified lysocellin product containing greater than 90% alkali metal lysocellin and less than 10% impurities in the form of fatty acids and fatty acid ester salts.

16. The process of claim 13 wherein the HCl is mixed with the lysocellin solids in amounts sufficient to produce a pH of between about 1 to 3.

17. The process of claim 13 wherein the HCl is mixed with the lysocellin solids in amounts sufficient to produce a pH of about 2.

18. The process of claim 13 wherein the NaOH is mixed with the lysocellin acid and fatty acid solids in amounts sufficient to produce a pH of about 12.

19. The process of claim 13 wherein the separating steps are filtration steps.

* * * * *